United States Patent [19]
Behan et al.

[11] Patent Number: 5,662,691
[45] Date of Patent: Sep. 2, 1997

[54] SYSTEM AND METHOD FOR IMPLANTING AN IMPLANTABLE CARDIAC DEVICE

[75] Inventors: Edgar G. V. Behan, Issaquah; David P. Finch, Bothell; Craig S. Siegman, Redmond, all of Wash.

[73] Assignee: InControl, Inc., Redmond, Wash.

[21] Appl. No.: 561,884

[22] Filed: Nov. 22, 1995

[51] Int. Cl.$^6$ .................................................. A61N 1/372
[52] U.S. Cl. ................... 607/32; 607/10; 607/36
[58] Field of Search .............................. 607/5, 9, 10, 30, 607/32, 36, 59, 60; 128/903

[56] References Cited

U.S. PATENT DOCUMENTS

| | | | |
|---|---|---|---|
| 4,550,731 | 11/1985 | Batina et al. | 128/903 |
| 4,958,632 | 9/1990 | Duggan | 607/30 |
| 5,154,169 | 10/1992 | Miyata et al. | 607/10 |
| 5,304,209 | 4/1994 | Adams et al. | 607/36 |
| 5,336,245 | 8/1994 | Adams et al. | 607/32 |
| 5,339,821 | 8/1994 | Fujimoto | 128/903 |

Primary Examiner—William E. Kamm
Assistant Examiner—George R. Evanisko
Attorney, Agent, or Firm—Richard O. Gray, Jr.

[57] ABSTRACT

A system for use in implanting an implantable cardiac device includes an external device operable to emulate the operation of the implantable cardiac device in accordance with a set of modality and operating parameters. An external programmer includes a transmitter for transmitting the set of operating and modality parameters and the external device includes a receiver for receiving the set of operating parameters transmitted by the external programmer. A memory within the external programmer stores the transmitted set of operating parameters and retransmits the set of operating parameters to the implantable cardiac device after it is implanted. The external programmer and external device each include a telemetry antenna. The external programmer and external device are arranged for aligning the telemetry antennas when the external programmer and external device are being used together. The external programmer further includes a control panel arrangement which enables convenient control panel positioning by an implanting physician.

2 Claims, 4 Drawing Sheets

SYSTEM AND METHOD FOR IMPLANTING AN IMPLANTABLE CARDIAC DEVICE

BACKGROUND OF THE INVENTION

The present invention generally relates to a system and method for implanting an implantable cardiac device. The present invention more particularly relates to such a system and method wherein programmable parameters are conveyed to an external device from an external programmer to establish proper operating functionality consistent with the patient's requirements. After the implantable cardiac device is implanted, the last set of programmable parameters provided to the external device by the programmer are conveyed from the programmer to the implanted device. The external device and programmer are configured to permit physical separation of the external device and programmer during utilization or to permit the external device and programmer to be combined in a predetermined relation to form a single unit. In either configuration, telemetry between the external device and the programmer is supported by properly orientated and aligned telemetry antennas of the programmer and the external device to permit reliable telemetry of the programmable parameters. The programmer also includes a parameter selection panel which is hingedly coupled to a top wall of the programmer to permit the same to be raised into a convenient position during use.

The implantation in human patients of implantable cardiac devices such as pacemakers and cardioverters/defibrillators has been on going for many years. Such devices are implanted beneath the skin of a patient and include or are associated with a lead system comprising one or more endocardial, intravascular, or subcutaneous leads. Each lead includes at least one electrode for making electrical contact with the patient's heart. Such electrical contact permits heart activity to be sensed and/or electrical therapeutic energy, such as pacing or cardioversion pulses, to be applied to the heart by the implanted cardiac device.

To implant such a device, the lead system is first implanted beneath the skin of the patient. Then, an external device, not suitable for implantation, but which can fully emulate the diagnostic and therapeutic functionality of the device to be implanted, is directly coupled to the implanted lead system. Modern day implantable cardiac devices can be extremely complex in offering multiple modes of operation and a myriad of selectable functional parameters. With the external device, the various modes of device operation and combinations of functional parameters can be manually selected for interaction with the patient for evaluation before the implantable device is actually implanted.

Modern day implantable cardiac devices are also generally able to communicate with an external programmer through a telemetry system. To that end, the programmer will have telemetry capability to transmit the programmable parameters and modes to the implanted device. The telemetry system generally includes a transmitter for transmitting, by way of radio frequency (RF) energy, selectable modality data and operational parameter data to the implanted device. The implanted device in turn has telemetry capability including a receiver for receiving the mode and parameter data transmitted by the programmer for enabling the selected modes of operation and implementing the selected parameters in the implanted device. To accomplish this last step, it is necessary for the implanting physician to manually transfer the selected modes and parameters from the external device to the programmer for transmission to the implanted device. This procedure is not only cumbersome and inconvenient, there is also always the potential for human error during the transference. This can result in the implanted device being set in improper modes or with improper operating parameters.

In addition to the foregoing, it is desirable to render the programmer and external device combination as physically convenient to use as possible. This is desirable given the rather busy operating room environment which normally prevails during the implantation of an implantable cardiac device.

The present invention provides an improved system for implanting an implantable cardiac device which addresses the foregoing issues. By virtue of the present invention, the transfer of mode and functional parameter data from a programmer to the cardiac device after implantation is rendered advantageously more convenient and essentially error free. Also, an improved programmer and external device configuration allows the programmer to be placed in such engaged relation to the external device so as to form a single unit or permits the programmer and external device to be displaced from one another to provide extreme flexibility in arranging the combination within the operating room environment. Lastly, an improved mode and parameter selection panel configuration is hingedly coupled to a front or forward edge of the programmer so that mode and parameter selection may be made with minimum effort and maximum convenience.

SUMMARY OF THE INVENTION

The present invention provides a system for use in implanting an implantable cardiac device. The system includes an external device operable in accordance with a set of operating parameters for emulating the operation of the implantable cardiac device and an external programmer for providing the set of operating parameters. The external programmer includes a transmitter for transmitting the set of operating parameters and a receiver within the external device for receiving the set of operating parameters transmitted by the external programmer.

The invention further provides a method of implanting an implantable cardiac device beneath The skin of a patient. The method includes the steps of associating a lead system with at least one chamber of the patient's heart beneath the skin of the patient, providing an external device capable of operation in accordance with a set of operating parameters for emulating the operation of the implantable cardiac device, the external device having a receiver for receiving the operating parameters, and coupling the external device to the lead system. The method includes the further steps of transmitting a set of operating parameters to the external device to render the external device operational, storing a predetermined set of operating parameters transmitted to the external device, implanting the implantable cardiac device beneath the patient's skin, coupling the implanted cardiac device to the lead system, and transmitting the stored set of operating parameters to the implanted device.

The present invention further provides an external programmer for transmitting operating parameters to an implanted cardiac device. The external programmer includes an enclosure having a front panel and a rear panel defining a depth dimension, a pair of opposed side panels defining a width dimension, and opposed bottom and top panels substantially parallel to each other and transverse to the front, rear and side panels. The external programmer further includes a substantially planar operating parameter select means for permitting the operator to select operating parameters to be transmitted. The parameter select means is pivotably coupled to the top panel adjacent to the front panel and moveable from a lowered position overlying and substantially parallel to the top panel to a raised position at an acute angle to the top panel. A retaining means retains the parameter select means in a raised position.

DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like reference numerals identify identical elements and wherein:

DETAILED DESCRIPTION OF THE PREFERRED EMBODIMENT

Figure 1:
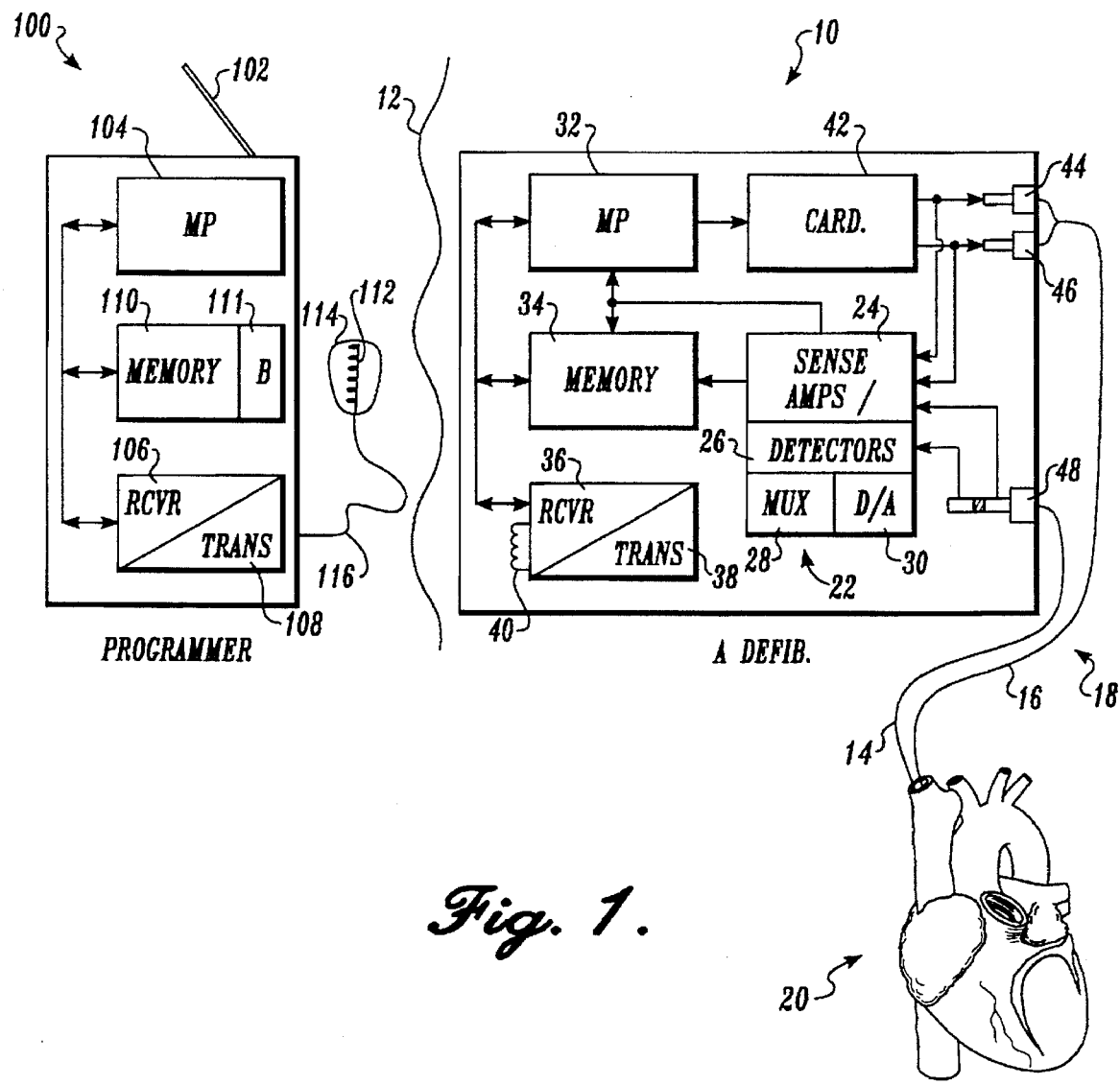
FIG. 1 is a blocked diagram of a programmer embodying the present invention and an implantable device which has been implanted beneath the skin of a patient in accordance with the present invention.

Referring now to FIG. 1, it illustrates an implantable atrial defibrillator 10 and an external programmer 100 embodying the present invention. The atrial defibrillator 10 is illustrated as having been implanted beneath the skin 12 of a patient. While the present invention may be applied to the implantation of most any type of implantable cardiac device, such as, for example, pacemakers, monitors, or defibrillators/cardioverters, the preferred embodiment herein will, for illustration, be directed to the implantation of an implantable automatic atrial defibrillator.

The atrial defibrillator 10 includes an implantable lead system 18 including an endocardial lead 14 and an intravascular lead 16. As fully described in U.S. Pat. No. 5,350,414, entitled LEAD SYSTEM FOR USE WITH AN ATRIAL DEFIBRILLATOR AND METHOD, which patent is issued to the assignee of the present invention and incorporated herein by reference, the endocardial lead 14 may be provided with tip and ring electrodes for placement in the right ventricle of the heart 20 and the intravascular lead 16 may be provided with an elongated distal electrode for placement in the coronary sinus or great cardiac vein of the heart 20 and an elongated proximal electrode for placement in the right atrium of the heart 20. The elongated electrodes of the intravascular lead 16 perform the dual function of sensing atrial activity of the heart and applying cardioverting electrical energy across the atria of the heart. The electrodes of the endocardial lead 14 provide sensing of ventricular activity of the heart in the right ventricle.

As also described in U.S. Pat. No. 5,458,621, issued Oct. 17, 1995 for AUTOMATIC GAIN CONTROL AND METHOD FOR ENABLING DETECTION OF LOW AND HIGH AMPLITUDE DEPOLARIZATION ACTIVATION WAVES OF THE HEART AND ATRIAL DEFIBRILLATOR UTILIZING THE SAME, and which patent is assigned to the assignee of the present invention and incorporated herein by reference, the atrial defibrillator 10 may further include sense channel circuitry 22 including a plurality of sense amplifiers 24 to form three different sense channels. These sense channels may include two sense channels for sensing ventricular activity of the heart and a third sense channel for sensing atrial activity of the heart. The atrial defibrillator 10 may further include a plurality of cardiac event detectors 26. The detectors 26 detect R waves in each of the ventricular activity sense channels and atrial events in the atrial activity sense channel.

The detection of atrial events supports atrial fibrillation detection. One such atrial fibrillation detector is fully described in co-pending U.S. Application Ser. No. 08/233,251, now U.S. Pat. No. 5,522,852 filed Apr. 26 1994 in the names of Harley G. White and Joseph M. Bocek for SELECTIVE CARDIAC ACTIVITY ANALYSIS ATRIAL FIBRILLATION DETECTION SYSTEM AND METHOD AND ATRIAL DEFIBRILLATOR UTILIZING THE SAME. Another such detector is fully described in co-pending U.S. application Ser. No. 08/278,055, now U.S. Pat. No. 5,486,199 filed Jul. 20, 1994 in the names of Jaeho Kim and Harley G. White for SYSTEM AND METHOD FOR REDUCING FALSE POSITIVES IN ATRIAL FIBRILLATION DETECTION. Both of the aforementioned co-pending applications are assigned to the assignee of the present invention and incorporated herein by reference.

The R wave detection supports cardioversion synchronization as described, for example, in co-pending U.S. application Ser. No. 08/259,476, now U.S. Pat. No. 5,584,864 filed Jun. 14, 1994 in the name of Harley G. White for CARDIOVERSION SYNCHRONIZATION SYSTEM AND METHOD FOR AN ATRIAL DEFIBRILLATOR, which is assigned to the assignee of the present invention and incorporated herein by reference. The aforementioned co-pending application discloses a synchronization system which includes two ventricular sense channels and requires that an R wave be sensed in both channels before the energy may be applied. In addition, other synchronization criteria may be required to be satisfied such as a minimum interval criteria as described, for example, in Adams, et al., U.S. Pat. No. 5,207,219, which issued on May 4, 1993 for ATRIAL DEFIBRILLATOR AND METHOD FOR PROVIDING INTERVAL TIMING PRIOR TO CARDIOVERSION, and which patent is assigned to the assignee of the present invention and incorporated herein by reference.

The atrial defibrillator 10 further includes a microprocessor 32 and a memory 34. The microprocessor controls the overall functioning of the atrial defibrillator under operating parameters and instructions stored in the memory 34. In addition to storing operating parameters and instructions, the memory also stores process electrogram data for processing and electrogram data for telemetry. The electrogram data stored in the memory 34 are acquired from electrograms generated by the three sense channels. The electrograms are multiplexed by a multiplexor 28 and converted to digital samples by a digital-two-analog converter 30.

A receiver 36 and a transmitter 38 within the atrial defibrillator 10 form a telemetry system which receives programmable parameters from the external programmer 100 and transmits data, such as electrogram data to the external non-implanted programmer 100. The telemetry system preferably takes the form of the telemetry system fully described in U.S. Pat. No. 5,342,408, issued Aug. 30, 1994, for TELEMETRY SYSTEM FOR AN IMPLANTABLE CARDIAC DEVICE, which patent is assigned to the assignee of the present invention and incorporated herein by reference. A coil antenna is shared by the receiver 36 and transmitter 38 for both reception and transmission respectively.

The atrial defibrillator 10 further includes a cardioverting stage 42. When atrial fibrillation is detected, a storage capacitor within the stage 42 is charged to a selected peak voltage. Thereafter, upon successful completion of a synchronization protocol, the cardioversion stage 42 discharges a portion of the energy stored in the storage capacitor. The discharged energy is applied to the elongated electrodes of the intravascular lead 16 for applying the cardioverting electrical energy to the atria of the heart 20.

The external programmer 100 includes a substantially planar operating parameter selection panel 102, a microprocessor 104, a receiver 106, a transmitter 108, and a memory 110. The memory 110 includes an updateable buffer portion (B) 111 for storing a predetermined set of mode and operating parameter data as will be described hereinafter. The receiver 106 and transmitter 108 share a coil antenna 112 which is confined within a programmer wand 114. The antenna 112 is coupled to the programmer 100 by a cable 116 to permit the wand to be held over the implant site to align antenna 112 with the antenna 40 of the implanted defibrillator 10 as also disclosed in the aforementioned U.S. Pat. No. 5,342,408.

The microprocessor 104 controls the overall function of the programmer 100, responsive to operating instructions stored in memory 110. The memory 110 also stores operating parameters for the defibrillator which are selected from the parameter selection panel 102 and stored in the buffer 111. When these parameters are to be transmitted to the implanted defibrillator after it is implanted, they are obtained from the buffer 111 and transmitted to the defibrillator to provide it with its programmable parameters and modal functionality.

Lastly, the lead system 18 includes a plurality of male connectors 44, 46, and 48. The connectors are received by corresponding female receptacles of the defibrillator 10 to permit the electrodes of leads 14 and 16 to make electrical contact with the inner circuitry of the defibrillator 10 while establishing a hermetical seal for the interior of the defibrillator 10, as is well known in the art.

Figure 2:
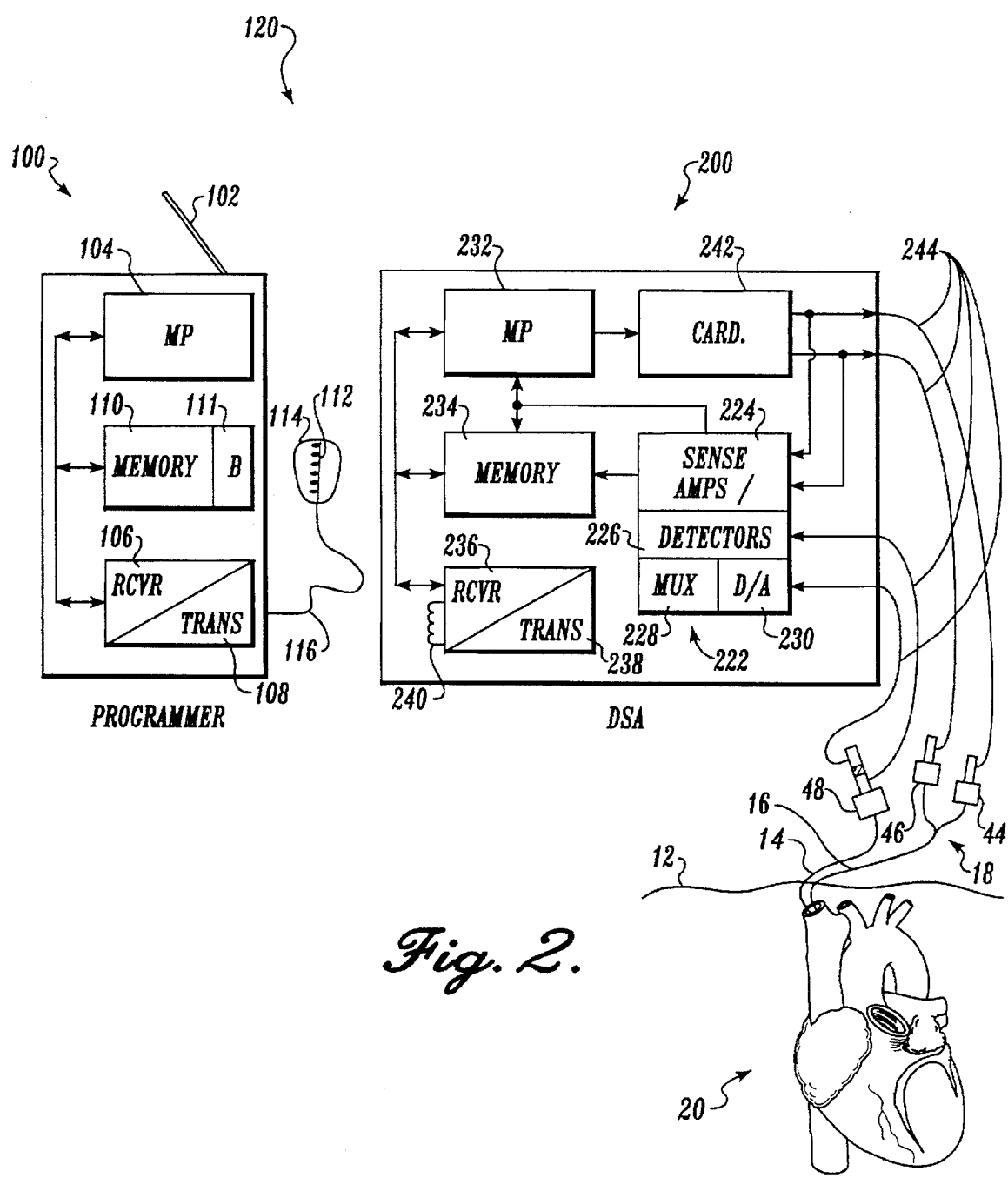
FIG. 2 is a blocked diagram of system embodying the present invention including the programmer of FIG. 1 and an external device for use in implanting the implantable cardiac device of FIG. 1.

Referring now to FIG. 2, it illustrates the programmer 100, as previously described with reference to FIG. 1, and an external device 200. The programmer 100 and external device 200 form a system 120 embodying the present invention for use in implanting an implantable cardiac device such as the atrial defibrillator 10 of FIG. 1.

The external device 200 fully emulates the functionality of the atrial defibrillator 10 of FIG. 1 and will hereinafter be referred to herein as the defibrillation system analyzer (DSA). To emulate the functionality of the atrial defibrillator 10 of FIG. 1, the DSA 200 includes essentially identical software, circuit components, and circuit configuration as the atrial defibrillator 10. The only exception to the foregoing may be enabling the DSA to deliver a higher peak cardioverting voltage than the implantable device is capable of providing.

To the end of emulating the operation of the implantable atrial defibrillator, through comparison of the DSA block diagram of FIG. 2 to the implantable atrial defibrillator block diagram of FIG. 1, it can be observed that the circuit components and configuration are essentially identical. Like the defibrillator 10, the DSA 200 includes sense channel circuitry 222 including sense amplifiers 224, cardiac event detectors 226, multiplexor 228, and digital to analog converter 230. The DSA 200 further includes microprocessor 232, memory 234, receiver 236, transmitter 238, and coil antenna 240. All of the foregoing circuit components preferably function in the identical manner as the circuitry of the atrial defibrillator 10 of FIG. 1. Hence, the previous functional description of the same may be referred for a description of the manner of preferred operation of the DSA 200.

The DSA 200 further includes a patient cable 244 of the type well known in the art for connecting the internal circuitry of the DSA 200 to the appropriate contacts of connectors 44, 46, and 48 to in turn connect the interior circuitry of the DSA 200 to the proper electrodes of the lead system 18. The cable 244 may make electrical connection to the contacts of the connectors 44, 46, and 48 through alligator clips (not shown) as is known in the art.

In accordance with the present invention, when the atrial defibrillator 100 of FIG. 1 is to be implanted beneath the skin 12 of the patient, the lead system 18 is first implanted as previously described. The DSA 200 is then coupled, through the patient cable 244, to the lead system 18 as illustrated in FIG. 2.

Once the DSA 200 is coupled to the lead system 18, the wand 114, and hence the coil antenna 112, of the programmer is aligned with the coil antenna 240 of the DSA. This may be accomplished as is more particularly described hereinafter with reference to FIGS. 3 and 4. Next, the programmer is energized and the parameter selection panel 102 is accessed to initiate a command from the programmer which is transmitted by transmitter 108 to the DSA receiver 236 to cause the DSA to be energized. To render the DSA with maximum flexibility for use, it is preferably battery powered. However, since the DSA is not an implantable device, the battery to power the DSA may be many times larger then the battery which powers the implantable device.

Once, the DSA is energized, the parameter select panel 102 is used to initiate and transmit operating parameters and further commands to the DSA 200 under an implant protocol until the physician is satisfied that the appropriate modalities and operating parameters necessary to meet the needs of the patient's heart condition are derived. During this process, the updateable buffer portion (B) 111 of memory 110 is provided with the latest modality and parametric data utilized by the physician. Hence, at any one time, the buffer 111 will contain the complete latest set of modality and parametric data used by the physician in defining the functionality or operation of the DSA 200 out of the myriad number of possible and available sets of modality and parametric data.

The DSA is next uncoupled from the lead system 18 and the atrial defibrillator 10 is implanted and coupled to the lead system 18 as illustrated in FIG. 1. The programmer wand 114 is then positioned over the implant site and the atrial defibrillator 10 is energized by the programmer so that the antennas 112 and 40 may be aligned. As previously mentioned, this is preferably accomplished as described in the aforementioned U.S. Pat. No. 5,342,408 which is assigned to the assignee of the present invention and incorporated herein by reference.

Once the defibrillator 10 is energized, the atrial defibrillator 10 may now be provided with an initial set of operating modality and parametric data. To that end, through the control panel 102, the microprocessor is caused to access the data in buffer 111. The data is transferred to the transmitter 108 which then retransmits the modality and parametric data stored in buffer 111, this time to the receiver 36 of the defibrillator 10. Once received, the data is stored in predetermined locations of memory 34.

Now that the last set of modality and parametric data used by the physician in operating the DSA 200 have been transferred to the memory 34 of the atrial defibrillator 10, the atrial defibrillator will now function in the same manner as the DSA last functioned under the control of the physician.

Alternatively, the set of modality and parametric data transferred to the atrial defibrillator 10 may be other than the last set used by the physician in controlling the DSA. For example, the physician may wish to store in the buffer 111 different sets of operating data for comparison purposes while utilizing the DSA 200 and then transmit a preferred one of the sets of operating data to the atrial defibrillator. What is important to note is that the transfer is accomplished automatically without the potential for human error.

Figure 3:
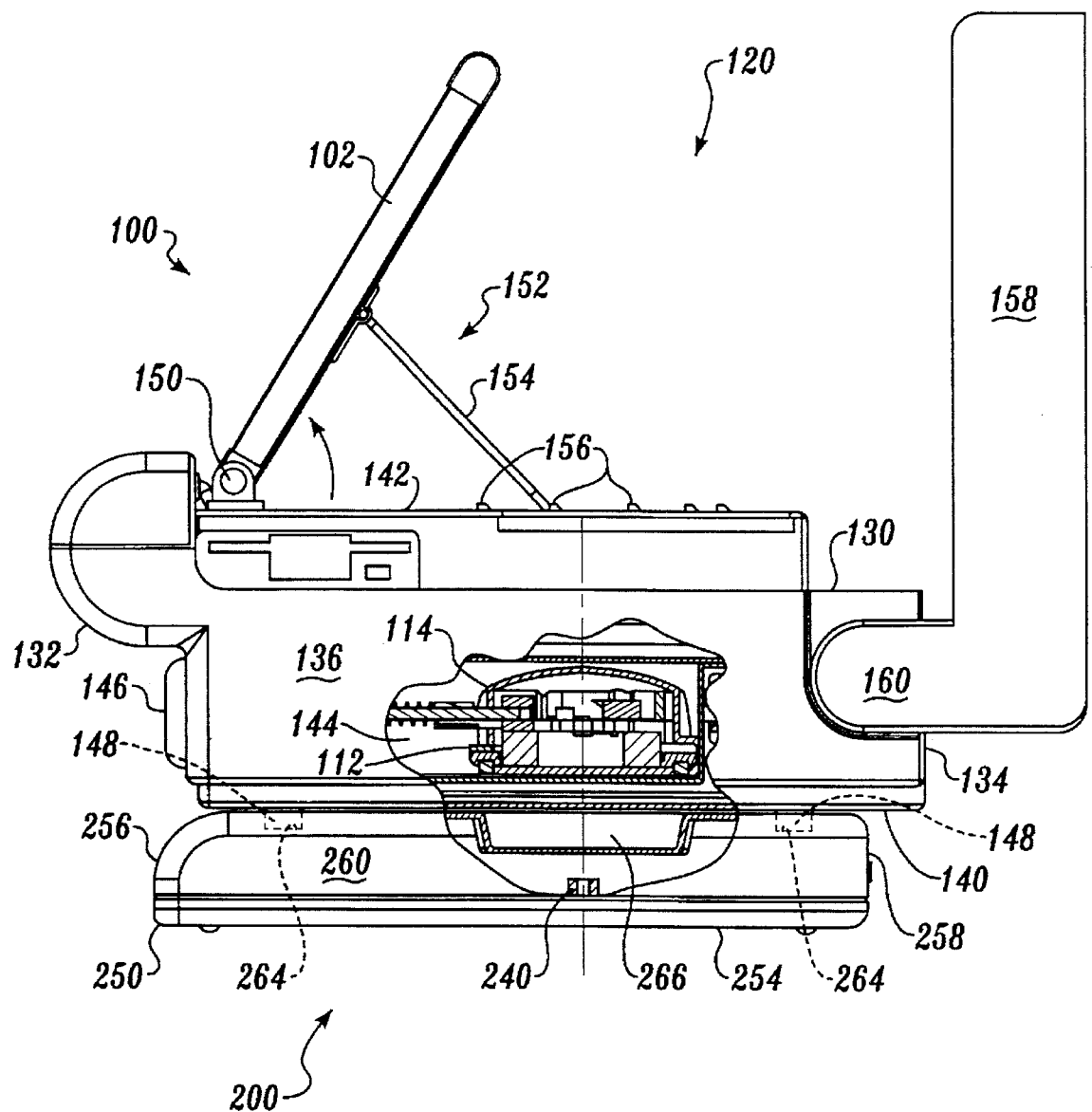
FIG. 3 is a side plan view, partly in cross-section and partly cut away of a programmer embodying the present invention and an external device embodying the present invention wherein the programmer is arranged on top of the external device to form a single unit in accordance with one aspect of the present invention.
Figure 4:
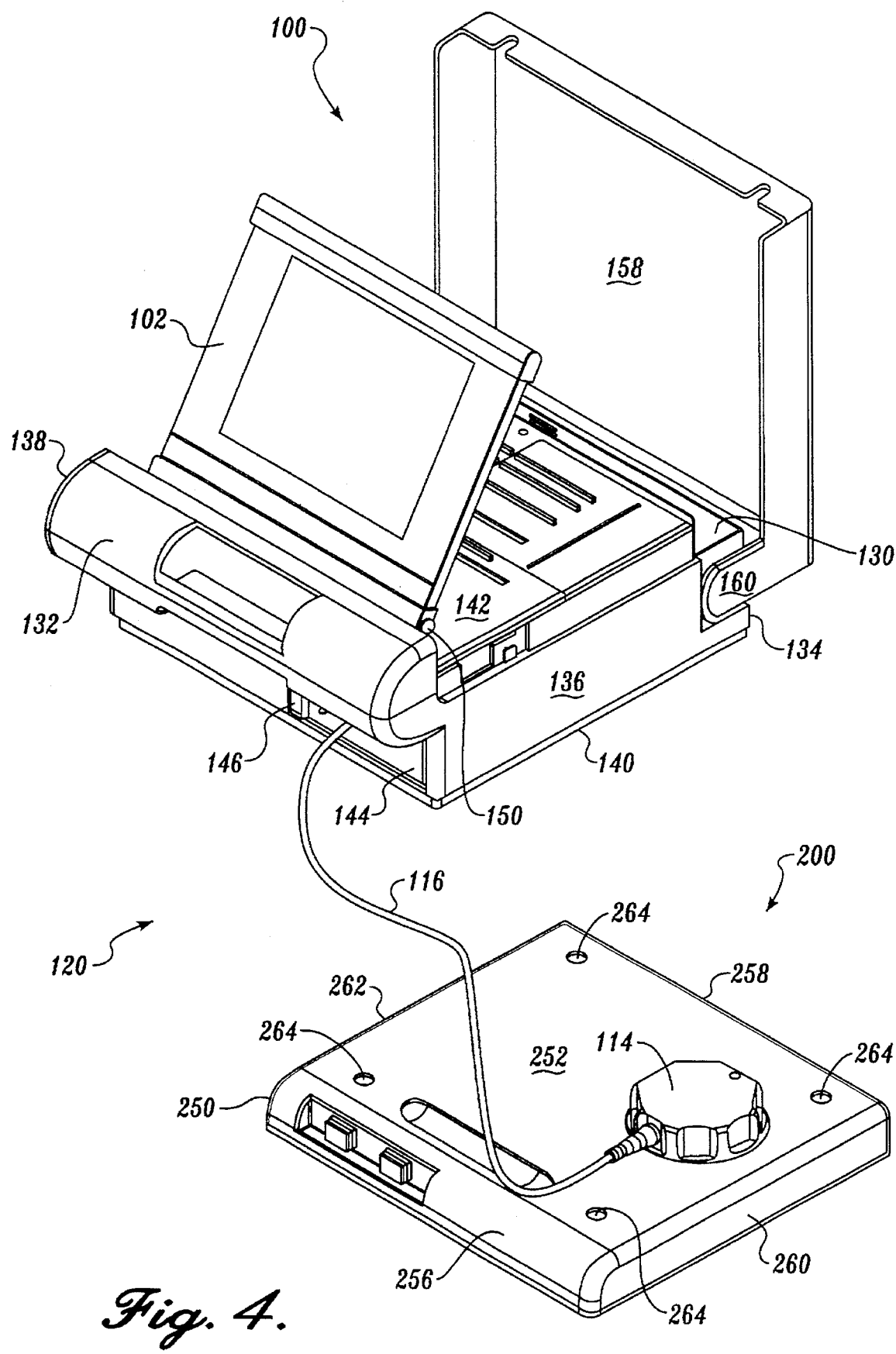
FIG. 4 is a perspective view of the programmer and the external device of FIG. 3 shown in spaced apart relation while maintaining cooperative operation in accordance with another aspect of the present invention.

Referring now to FIGS. 3 and 4, the prospective views there shown illustrate the programmer 100 and DSA 200 in two different preferred configurations for use. As illustrated in FIG. 3, the programmer 100 is engaged on top of the DSA 200 so as to form a single unit. As illustrated in FIG. 4, the programmer 100 and DSA 200 are displaced from one another. However, as will be seen hereinafter, the programmer and DSA are still in communicative relation to each other.

As will be noted in FIGS. 3 and 4, the programmer 100 includes an enclosure 130 having a front panel 132 and a rear panel 134 defining a depth dimension, a pair of opposed side panels 136 and 138 defining a width dimension, and opposed bottom and top panels 140 and 142 respectively. The top and bottom panels 140 and 142 are substantially parallel to each other and are substantially transversed to the front, rear, and side panels 132, 134, 136, and 138 respectively.

Similarly, the DSA includes a housing 250 having a top surface 252, a bottom surface 254, a front panel 256, and a rear panel 258, and a pair of side panels 260 and 262. The top and bottom surfaces 252 and 254 are substantially parallel to each other and are substantially transverse to the front, rear, and side panels 256, 258, 260 and 262 respectively.

The enclosure 130 of programmer 100 includes an inner compartment 144 for stowing the programmer wand 114 in a predetermined position within the programmer enclosure 130. The wand 114 which encloses the programmer coil antenna 112 may be removed from the enclosure 130 through a sliding door 146 which forms part of the front panel 132.

The programmer further includes a plurality of pendent projections 148 which extend from the bottom panel 140. Correspondingly, the top surface 252 of the DSA housing 250 includes a like plurality of recesses 264. The projections 148 and recesses 264 form alignment means and are arranged so as to be in aligned relation to permit the recesses 264 to receive the projections 148 when the programmer 100 is placed on top and immediately adjacent to the DSA. As a result, the programmer 100 and DSA 200, when so configured as seen in FIG. 3, form a single interlocked unit.

In addition, as may also be noted in FIG. 3, the DSA coil antenna 240 is located at a predetermined position within the housing 250. The stowed position of the wand 114 defined by the compartment 144 and the position of the DSA antenna 240 within the housing 250 are in such relation to each other and the projections 148 and recesses 264, so that when the programmer is placed on top of the DSA with the recesses 264 receiving the projections 148, the antennas 112 and 240 will also be in a aligned relation to enable reliable telemetry transmission between the programmer 100 and DSA.

It will also be noted in FIG. 3 that the DSA 200 also includes another recess 266 within the housing top surface 252 and which is positioned immediately above the DSA coil antenna 240. The recess 266 is dimensioned for receiving the programmer wand 114 as may be seen in FIG. 4. In FIG. 4, the wand 114 has been removed from its stowage compartment 144 and placed in the recess 266. This aligns the antenna 112 within the wand 114 with the DSA coil antenna 240 to support reliable telemetry between the programmer 100 and DSA 200 while allowing the programmer 100 and DSA 200 to be displaced from one another for maximum flexibility in the operating room environment.

As will be further noted in FIGS. 3 and 4, the parameters selection panel 102 is pivotably coupled to the programmer top panel 142 at a pivot connection 150 adjacent to the front panel 132. This permits the panel 102 to be moveable from a lowered position overlying and substantially parallel to the top panel 142 to a raised position at an acute angle θ to the top panel as best seen in FIG. 3. A retaining means 152 including a pendant member 154 and a plurality of ribs 156 formed in the top panel 142 permit the panel 102 to be retained at any one of a plurality of different acute angle positions relative to the top panel 142. This presents an extremely convenient and flexible arrangement for the physician in the operating room environment for positioning the panel 102. It also places the panel 102 towards the front of the programmer so that the physician does not need to reach to utilize the panel during modality and operating parameter selection.

Lastly, it will be further noted in FIGS. 3 and 4 that the programmer 100 further includes a cover panel 158. The cover panel 158 includes a pair of transverse extensions 160 which are pivotably connected to the side panels 136 and 138 adjacent to the rear panel 134. This permits the cover panel 158 to cover the parameter select panel 102 when the cover panel is lowered to close the programmer and permits the parameter select panel 102 to be pivoted to a raised position for use when the cover panel 158 is in a raised position as illustrated in FIGS. 3 and 4. The cover panel 158 may further be used to shade the panel 102 at low angle positions.

While particular embodiments of the present invention have been shown and described, modification may be made, and it therefore intended to cover in the appended claims all such changes and modifications which fall within the true spirit and scope of the invention.

What is claimed is:

1. A cardiac system comprising:
   an external device including means for operation responsive to a set of operating parameters;
   an external programmer for providing the set of operating parameters, the external programmer including transmitting means for transmitting the set of operating parameters; and
   receiving means within the external device for receiving the set of operating parameters transmitted by the external programmer,
   wherein the external programmer includes an enclosure, wherein said transmitting means includes a first antenna positionable at a first predetermined position within said enclosure, wherein said external device includes a housing, wherein said receiving means includes a second antenna positioned at a second predetermined position within said housing, wherein said enclosure and said housing include alignment means for aligning said enclosure and said housing in an aligned immediately adjacent relation to each other, and wherein said first antenna and second antenna are aligned with each other when said enclosure and said housing are in said aligned immediately adjacent relation, and wherein said housing includes a top surface, wherein said alignment means includes a plurality of recesses within said top surface, wherein said enclosure includes a bottom surface, wherein said alignment further includes a plurality of pendent projections extending from said bottom surface, and wherein said recesses receive said pendent projections to place said enclosure and said housing in said aligned immediately adjacent relation.

2. A cardiac system comprising:

an external device including means for operation responsive to a set of operating parameters;

an external programmer for providing the set of operating parameters, the external programmer including transmitting means for transmitting the set of operating parameters; and receiving means within the external device for receiving the set of operating parameters transmitted by the external programmer, wherein the external programmer includes an enclosure, wherein said transmitting means includes a first antenna positionable at a first predetermined position within said enclosure, wherein said external device includes a housing, wherein said receiving means includes a second antenna positioned at a second predetermined position within said housing, wherein said enclosure and said housing include alignment means for aligning said enclosure and said housing in an aligned immediately adjacent relation to each other, and wherein said first antenna and second antenna are aligned with each other when said enclosure and said housing are in said aligned immediately adjacent relation, and wherein said transmitting means further includes an antenna enclosure, said first antenna being within said antenna enclosure and said antenna enclosure being moveable externally from said enclosure, wherein said housing includes a recess adjacent said second antenna, and wherein said recess is dimensioned for receiving said antenna enclosure and positioned for aligning said first antenna with said second antenna.

* * * * *